(12) United States Patent
Storz

(10) Patent No.: US 6,909,003 B2
(45) Date of Patent: Jun. 21, 2005

(54) PROCESS FOR THE MANUFACTURE OF ORGANIC COMPOUNDS

(75) Inventor: Thomas Storz, Thousand Oaks, CA (US)

(73) Assignee: Novartis AG, Basel (CH)

( * ) Notice: Subject to any disclaimer, the term of this patent is extended or adjusted under 35 U.S.C. 154(b) by 70 days.

(21) Appl. No.: 10/428,257

(22) Filed: May 2, 2003

(65) Prior Publication Data

US 2003/0233001 A1 Dec. 18, 2003

(30) Foreign Application Priority Data

May 3, 2002 (GB) .............................................. 0210234

(51) Int. Cl.$^7$ ........................ C07C 59/10; C07C 29/143; C07D 213/00
(52) U.S. Cl. ........................ 546/152; 544/316; 548/469; 548/562; 546/339; 562/510; 564/123
(58) Field of Search .......................... 544/316; 546/152, 546/339; 548/469, 562; 562/510; 564/123

(56) References Cited

FOREIGN PATENT DOCUMENTS

EP          0 916 637          5/1999

OTHER PUBLICATIONS

Repič et al., "The Story of Lescol: From Research to Production", Organic Process Research and Development, vol. 5, pp. 519–527 (2001).

*Primary Examiner*—Zinna Northington Davis

(74) *Attorney, Agent, or Firm*—Paivi Kukkola

(57) ABSTRACT

The invention relates to a process for the manufacture of a compound of formula

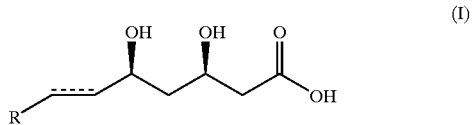

(I)

or a salt, especially a pharmaceutically acceptable salt with a base, thereof or a lactone thereof wherein the element ===== represents —CH$_2$—CH$_2$— or —CH=CH— and R represents a cyclic radical.

15 Claims, No Drawings

PROCESS FOR THE MANUFACTURE OF ORGANIC COMPOUNDS

The invention relates to a process for the manufacture of HMG-CoA reductase inhibitors, to process steps, to novel intermediates and to novel catalysts.

HMG-CoA reductase inhibitors (also called β-hydroxy-β-methylglutaryl-co-enzyme-A reductase inhibitors and also called statins) are understood to be those active agents which may be preferably used to lower the lipid levels including cholesterol in blood and can be used e.g. for the prevention or treatment of hyperlipidemia and artheriosclerosis.

The class of HMG-Co-A reductase inhibitors comprises compounds having differing structural features. For example, mention may be made of the compounds which are selected from the group consisting of atorvastatin, cerivastatin, fluvastatin, lovastatin, pitavastatin (formerly itavastatin), pravastatin, rosuvastatin, and simvastatin, or, in each case, a pharmaceutically acceptable salt thereof.

Preferred HMG-Co-A reductase inhibitors are those agents which have been marketed, most preferred is fluvastatin, atorvastatin, pitavastatin, especially the Calcium salt thereof, or simvastatin or a pharmaceutically acceptable salt thereof.

Atorvastatin of formula

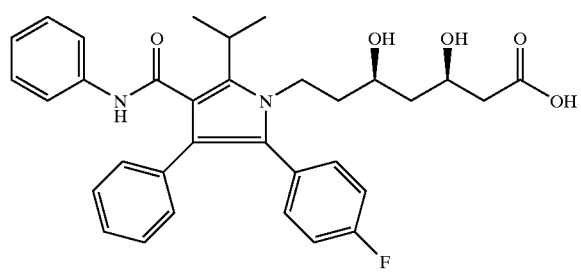

is disclosed and claimed in U.S. Pat. No. 5,273,995.

Cerivastatin of formula

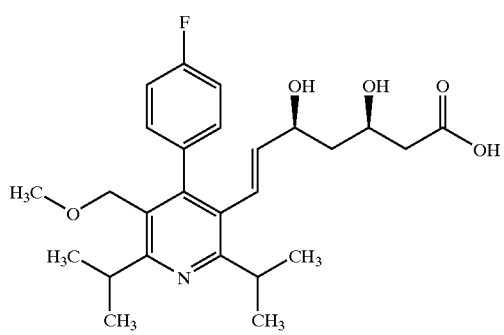

is disclosed and claimed in U.S. Pat. No. 5,177,080.

Racemic fluvastatin with syn-configuration of the hydroxy groups in formula

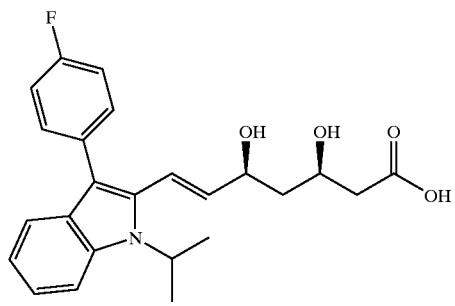

is disclosed and claimed in U.S. Pat. No. 5,345,772.

Lovastatin of formula

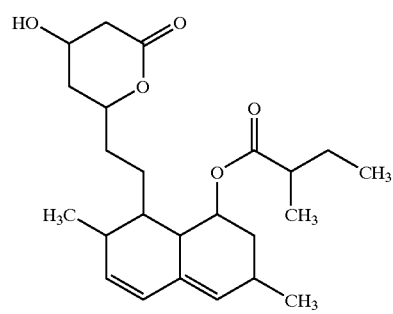

is disclosed and claimed in U.S. Pat. No. 4,231,938.

Pitavastatin of formula

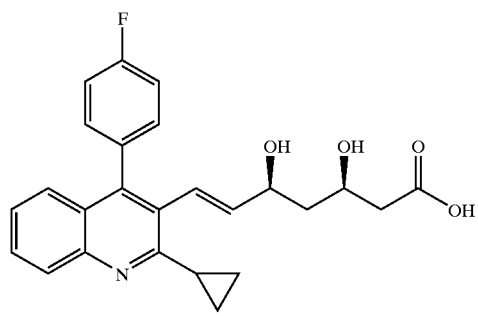

is disclosed and claimed in U.S. Pat. No. 5,856,336.

Pravastatin of formula

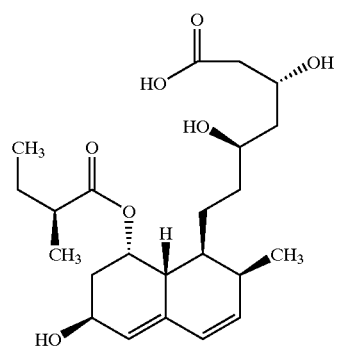

is disclosed and claimed in U.S. Pat. No. 4,410,629.

Rosuvastatin of formula

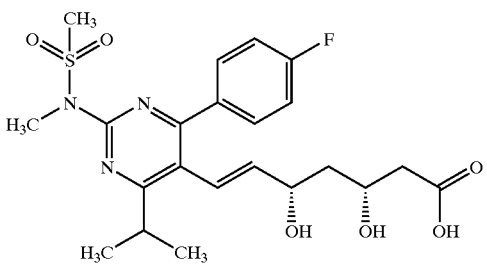

is disclosed and claimed in U.S. Pat. No. 5,260,440.

Simvastatin of formula

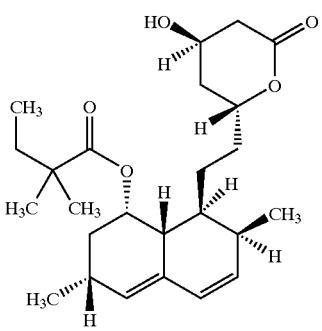

is disclosed and claimed in U.S. Pat. No. 4,444,784.

The structure of the active agents identified hereinbefore or hereinafter by generic or tradenames may be taken from the actual edition of the standard compendium "The Merck Index" or from databases, e.g. Patents International (e.g. IMS World Publications). The corresponding content thereof is hereby incorporated by reference. Any person skilled in the art is fully enabled to identify the active agents and, based on these references, and is likewise enabled to manufacture and test the pharmaceutical indications and properties in standard test models, both in vitro and in vivo.

The corresponding active ingredients or a pharmaceutically acceptable salts thereof may also be used in form of a solvate, such as a hydrate or including other solvents, used for crystallization.

Essentially, statins comprise a cyclic core element and a side chain element of formula (A) or (C)

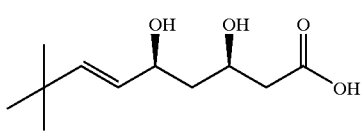

(A)

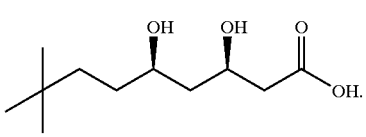

(C)

a 3,5-dihydroxy-hept-6-enoic acid moiety or a 3,5-dihydroxy-heptanoic acid moiety, respectively, each of which might form a corresponding lactone partial structure of formula (B) or (D)

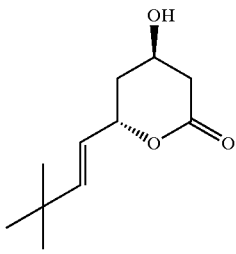

(B)

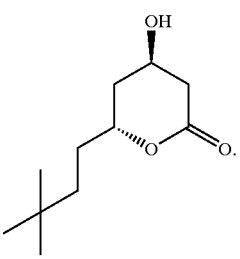

(D)

In said side chain elements (A) or (C), respectively, the 3,5-syn diol structure and the R-configuration at C-3 are essential features, as corresponding statins with this specific element exhibit the highest biological activity.

The objective of the present invention is to provide an enantioselective synthesis of compounds of formula (I) resulting in high yields and moreover guaranteeing a minimization of the ecological pollution of the environment, being economically attractive, e.g. by using less reaction steps in the reaction sequence for the manufacture of compounds of formula I, and leading to largely enantiomerically pure target products and to products of high crystallisability. Furthermore, another objective of the present invention is to provide a process that can be carried out in a larger scale and can thus be used for a corresponding production process. Furthermore, there is a need to avoid any separation of any stereoisomers.

Surprisingly, the process of the present invention clearly meets the above objectives. The process relates to an enantioselective synthesis by using essentially the so-called transfer hydrogenation approach. For example, an enantiomer excess (ee) of a compound of formula (I) of $\geq 95\%$, preferably $\geq 98\%$ and most preferably $\geq 99\%$ can be achieved.

The invention relates to a process for the manufacture of a HMG-CoA reductase inhibitory mevalonic acid derivative of formula (I)

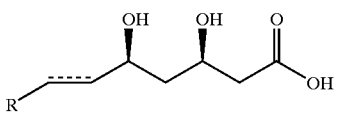

(I)

or a salt, especially a pharmaceutically acceptable salt with a base thereof, or a lactone thereof, wherein the element ═══ represents —$CH_2$—$CH_2$— or —CH═CH—, and R represents a cyclic residue.

A salt of a sound of formula (I) is, for example, a salt with a base, preferably a corresponding pharmaceutically acceptable salt thereof.

A lactone of a compound of formula (I) is represented by formulae (I a) and (I b)

(Ia)

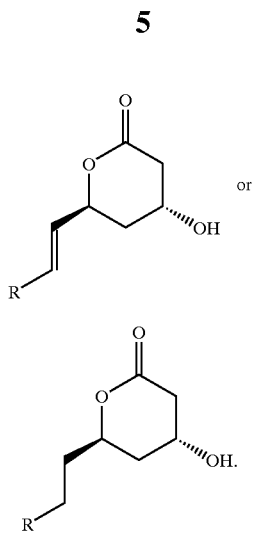

or (Ib)

Corresponding cyclic residue R comprises a cyclic residue selected from the group consisting of

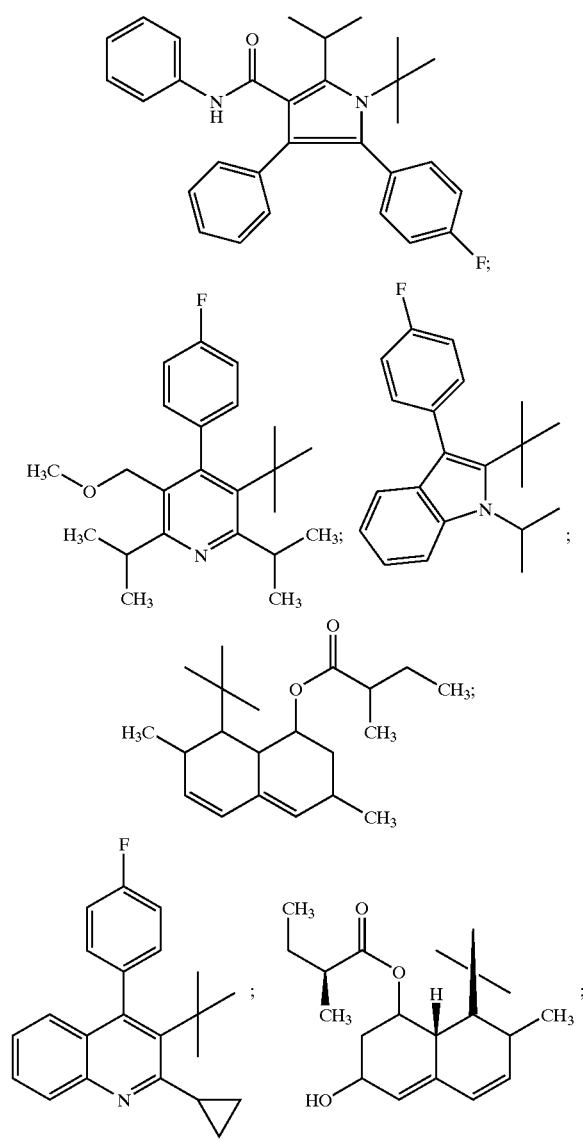

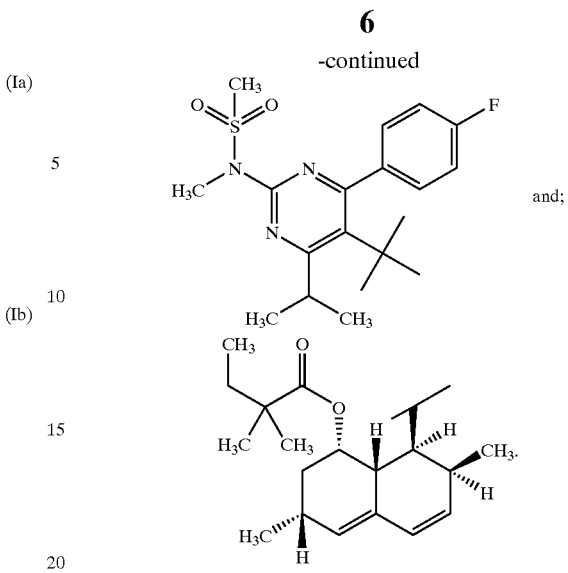

Extensive experimental evaluations surprisingly resulted in a process sequence for the manufacture that meets the above criteria showing the indicated advantages.

The process as disclosed in Bioorganic & Medicinal Chemistry Letters 9 (1999) 2977–2982 for the manufacture of pitavastatin (NKS 104) requires the formation of a racemic erythro-β,δ-dihydroxyester that is hydrolysed to form the corresponding acid. With α-methylbenzylamine a diastereomeric mixture of resulting salts is formed that need to be resolved into the different diastereomeric salts. The clear disadvantage of this approach is that half of the material needs to be distroyed. Accordingly, the process of the present invention can be carried out without such a diastereomeric resolution procedure.

The process for the manufacture of a compound of formula (I)

(I)

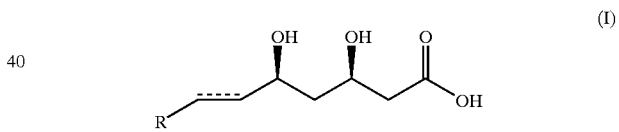

or a salt thereof, or a lactone thereof, wherein the element ═════ represents —CH$_2$—CH$_2$— or —CH═CH— and R represents a cyclic residue, according to the present inventions is characterized by (a) reacting a compound of formula (II a)

(IIa)

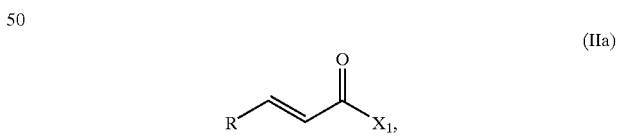

wherein R has the meaning as defined above and X$_1$ is an amino group substituted by C$_1$–C$_7$alkyl and C$_1$–C$_7$alkoxy; in the presence of a base with a compound of formula (II b)

(IIb)

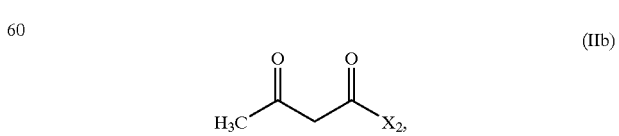

wherein X$_2$ represents substituted hydroxy or substituted amino; and (b) reducing a resulting compound of formula (II c)

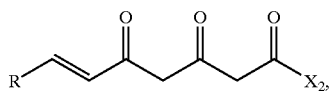
(IIc)

wherein R and $X_2$ have the meanings as defined above; in the presence of a hydrogen donor and a chiral Ru(II) catalyst selected from the group consisting of a compound of formulae (II d), (II d'), (II d''), and (II d''')

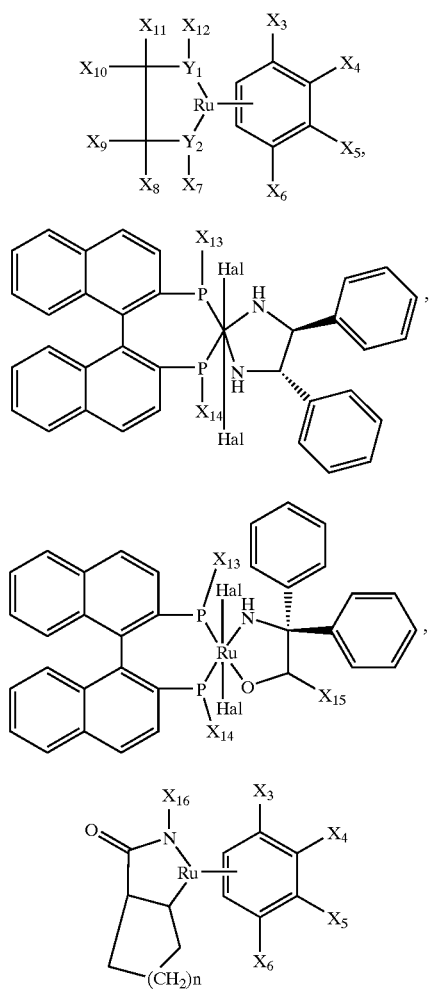

wherein $X_3$, $X_4$, $X_5$, and $X_6$, independently of one another, represents hydrogen, $C_1$–$C_7$alkyl, an araliphatic or aryl residue; one of $X_7$ and $X_{12}$ represents hydrogen, an aliphatic, cycloaliphatic, cycloaliphatic-aliphatic, aryl or araliphatic residue, araliphatyloxy, or araliphatylamino; and the other represents $SO_2$—$X_7'$ in which $X_7'$ is an aliphatic, cycloaliphatic, cycloaliphatic-aliphatic, aryl or araliphatic residue, araliphatyloxy, or araliphatylamino; $X_8$, $X_9$, $X_{10}$, and $X_{11}$, independently of one another, represents hydrogen, an aliphatic or cycloaliphatic residue, an araliphatic residue, aryl, acyl, aliphatyl-sulfonyl, or arylsulfonyl; Hal is halogen; $Y_1$ and $Y_2$ are nitrogen, or independently of one another, $Y_1$—$X_{12}$ and $Y_2$—$X_7$ may be replaced by oxygen $X_{13}$, and $X_{14}$, independently of one another, represents an aliphatic, a cycloaliphatic, a cycloaliphatic-aliphatic, an aryl or araliphatic residue; $X_{15}$ represents hydrogen, $C_1$–$C_7$alkyl, a cycloaliphatic, a cycloaliphatic-aliphatic, an araliphatic or an aryl residue; $X_{16}$ represents an aliphatic, a cycloaliphatic, a cycloaliphatic-aliphatic, an aryl or araliphatic residue or represents the structural element of formula $CH(X_{16}')(X_{16}'')$, wherein $X_{16}'$ represents $C_1$–$C_7$alkyl, an aryl or an araliphatic or a heteroaryl residue and $X_{16}''$ represents $C_1$–$C_7$alkyl, an aryl or an araliphatic residue or represents hydoxy, amino or mono- or di-substituted amino; and wherein, in each case, any (hetero)aromatic residue of a compound of formulae (II d), (II d'), (II d'') and (II d''') is unsubstituted or substituted; and (c) hydrolysing a resulting compound of formula (II e)

(IIe)

wherein R and $X_2$ have the meanings as defined above, and (d) isolating a resulting compound of formula (I) or a salt thereof;

and, if desired, converting a resulting free acid of formula (I) into a salt thereof or into a lactone of formula (I a) or (I b), respectively, or converting a resulting lactone of a formula (I a) or (I b) into an acid of formula (I) or a salt thereof, or converting a resulting compound of formula (I) wherein the element ⋯ represents —CH=CH— into a compound of formula (I) wherein the element ⋯ represents —CH$_2$—CH$_2$—.

The general terms used hereinbefore and hereinafter have the following meanings, unless defined otherwise.

$C_1$–$C_7$Alkyl is for example methyl, ethyl, n-propyl, isopropyl, n-butyl, isobutyl, sec-butyl, tert-butyl or a corresponding pentyl, hexyl or heptyl residue. $C_1$–$C_4$alkyl, especially methyl or tert-butyl, is preferred.

$C_1$–$C_7$Alkoxy is for example methoxy, ethoxy, n-propyloxy, isopropyloxy, n-butyloxy, isobutyloxy, sec-butyloxy, tert-butyloxy or a corresponding pentyloxy, hexyloxy, or heptyloxy residue. $C_1$–$C_4$alkoxy is preferred. Especially preferred is methoxy, and tert-butoxy.

Substituted hydroxy is, for example, an aliphatyloxy residue, in particular $C_1$–$C_7$alkyloxy, also $C_2$–$C_7$alkenyloxy or $C_2$–$C_7$alkynyloxy, an araliphatyloxy residue, in particular phenyl-$C_1$–$C_7$alkyloxy, also phenyl-$C_2$–$C_7$alkenyloxy or phenyl-$C_2$–$C_7$alkynyloxy. Especially preferred is Ethoxy.

Substituted amino is mono- or, independently of one another, di-substituted amino. Mono-substituted amino is, for example, monosubstituted by an aliphatic or araliphatic hydrocarbon radical. Especially preferred is methyl (S)-phenylethyl amino.

Di-substituted amino is, for example, amino that is, independently of one another, disubstituted by an aliphatic or araliphatic hydrocarbon radical or di-substituted by a divalent aliphatic hydrocarbon radical which may be interrupted by O or may be condensed at two adjacent carbon atoms with a benzene ring, in particular $C_2$–$C_7$ alkylene or $C_2$–$C_7$ alkyleneoxy-$C_2$–$C_7$alkylene. Especially preferred is diethylamino.

Examples of appropriately substituted amino groups which may be mentioned are $C_1$–$C_7$alkyl-, $C_2$–$C_7$alkenyl-, $C_2$–$C_7$alkynyl-, phenyl-$C_1$–$C_7$alkyl-, phenyl-$C_2$–$C_7$alkenyl-, phenyl-C–$C_7$-alkynyl-, di-$C_1$–$C_7$alkyl-, N-$C_1$–$C_7$alkyl-N-phenyl-$C_1$–$C_7$alkyl- and diphenyl-$C_1$–$C_7$alkylamino and also quinol-1-yl, isoquinol-2-yl, $C_2$–$C_7$alkylene- and $C_2$–$C_7$alkyleneoxy-$C_2$–$C_7$alkyleneamino.

An aliphatic residue is, for example, $C_1$–$C_7$alkyl, $C_2$–$C_7$alkenyl or secondarily $C_2$–$C_7$alkynyl. $C_2$–$C_7$Alkenyl is in particular $C_3$–$C_7$alkenyl and is, for example, 2-propenyl or 1-, 2- or 3-butenyl. $C_3$–$C_5$alkenyl is preferred.

$C_2$–$C_7$-Alkynyl is in particular $C_3$–$C_7$alkynyl and is preferably propargyl.

An araliphatic residue is in particular phenyl-$C_1$–$C_7$alkyl, also phenyl-$C_2$–$C_7$alkenyl or phenyl-$C_2$–$C_7$alkynyl. Especially preferred is benzyl.

An aryl residue is, for example, a carbocyclic or heterocyclic aromatic residue, in particular phenyl or in particular an appropriate 5- or 6-membered and monocyclic residue which has up to four identical or different hetero atoms, such as nitrogen, oxygen or sulfur atoms, preferably one, two, three or four nitrogen atoms, an oxygen atom or a sulfur atom. Appropriate 5-membered heteroaryl residues are, for example, monoaza-, diaza-, triaza-, tetraaza-, monooxa- or monothia-cyclic aryl radicals, such as pyrrolyl, pyrazolyl, imidazolyl, triazolyl, tetrazolyl, furyl and thienyl, while suitable appropriate 6-membered residues are in particular pyridyl.

Pyrrolyl is, for example, 2- or 3-pyrrolyl. Pyrazolyl is 3- or 4-pyrazolyl. Imidazolyl is 2- or 4-imidazolyl. Triazolyl is, for example, 1,3,5-1H-triazol-2-yl or 1,3,4-triazol-2-yl. Tetrazolyl is, for example, 1,2,3,4-tetrazol-5-yl, furyl is 2- or 3-furyl and thienyl is 2- or 3-thienyl, while suitable pyridyl is 2-, 3- or 4-pyridyl.

Any (hetero)aromatic residue is preferably unsubstituted or substituted, for example, by one or more, e.g. two or three, residues e.g. those selected from the group consisiting of $C_1$–$C_7$alkyl, hydroxy, $C_1$–$C_7$alkoxy, $C_2$–$C_8$alkanoyl-oxy, halogen, nitro, cyano, and $CF_3$.

A cycloaliphatic residue is, for example, a $C_3$–$C_8$cycloalkyl or, secondarily, $C_3$–$C_8$cycloalkenyl. $C_3$–$C_8$Cycloalkyl is, for example, cyclopropyl, cyclobutyl, cyclopentyl, cyclohexyl and cycloheptyl. Cyclopentyl and cyclohexyl are preferred.

$C_3$–$C_8$Cycloalkenyl is in particular $C_3$–$C_7$cycloalkenyl and is preferably cyclopent-2-en-yl and cyclopent-3-enyl, or cyclohex-2-en-yl and cyclohex-3-en-yl.

A cycloaliphatic-aliphatic residue is, for example, $C_3$–$C_8$cycloalkyl-$C_1$–$C_7$alkyl, preferably $C_3$–$C_6$-cycloalkyl-$C_1$–$C_4$alkyl. Preferred is cyclopropylmethyl.

An araliphatyloxy residue is in particular phenyl-$C_1$–$C_7$alkyloxy, also phenyl-$C_2$–$C_7$alkenyloxy or phenyl-$C_2$–$C_7$alkynyloxy.

An araliphatylamino residue is in particular phenyl-$C_1$–$C_7$alkylamino, also phenyl-$C_2$–$C_7$alkenylamino or phenyl-$C_2$–$C_7$alkynylamino.

An acyl residue is, for example, $C_2$–$C_8$alkanoyl. $C_2$–$C_8$Alkanoyl is in particular acetyl, propionyl, butyryl, isobutyryl or pivaloyl. $C_2$–$C_5$Alkanoyl is preferred.

An (ar)aliphatyl-sulfonyl residue is, for example, $C_1$–$C_7$alkansulfonyl. $C_1$–$C_4$ Alkanesulfonyl is preferred. Especially preferred is benzylsulfonyl and (+)-camphersulfonyl.

An arylsulfonyl is in particular unsubstituted or substituted phenyl-sulfonyl or thiophensulfonyl. Especially preferred is p-cyanophenyl, 2-thiophensulfonyl.

The reactions described above and below in the variants are carried out, for example, in the absence or, customarily, in the presence of a suitable solvent or diluent or a mixture thereof, the reaction, as required, being carried out with cooling, at room temperature or with warming, for example in a temperature range from about –80° C. up to the boiling point of the reaction medium, preferably from about –10° to about +200° C., and, if necessary, in a closed vessel, under pressure, in an inert gas atmosphere and/or under anhydrous conditions.

Preferably, in the process according to the present invention compounds of formulae (II b), (II c) or (II e) are used, wherein $X_2$ is substituted amino, especially diethylamino.

Step (a):

In reaction Step (a), the reaction of a compound of formula (II a) with a compound of formula (II b) is carried out in a suitable inert solvent, such as diethylether, or tetrahydrofurane or acetonitrile, or dioxane.

Preferred is the reaction of a compound of formulae (II a) and (II b), wherein $X_2$ is substituted amino. It has surprisingly been found that the resulting compounds of formula (II c) exhibit a significantly better stability versus compounds of formula (II c), wherein $X_2$ is substituted hydroxy. Furthermore, compounds of formula (II c), wherein $X_2$ is substituted amino, show significant improved crystallisation properties versus compounds of formula (II c), wherein $X_2$ is substituted hydroxy. In view of these improved properties, corresponding compounds of formula (II c) are better qualified as starting material for reaction Step (b).

The present invention likewise relates to process Step (a).

Step (b):

Reaction Step (b) is an asymmetric transfer hydrogenation when using a chiral Ru(II) catalyst of formula (II d), (II d'), (II d") or (II d''') and a hydrogen donor.

Step (b) is carried out in a suitable inert solvent, such as an ether, e.g. tetrahydrofuran, an ester, such as ethylacetate, a nitrile, especially acetonitrile, or an amide, especially dimethylformamide, or a halogenoalkane, especially dichloromethane, and in a temperature range from, for example, from –78° C., to the boiling point of the solvent, preferably at room temperature or at 40–50° C.

Preferred Ru (II) catalysts of formula (II d) are those wherein $Y_1$ and $Y_2$ each are nitrogen, and $X_{10}$ and $X_9$ are part of an (ar)aliphatic ring system. Especially preferred are the (S,S)- or the (R,R)-enantiomer of 1,2-diaminocyclohexane as chiral ligand for the said catalyst, which, if desired, may also be formed in situ.

A preferred hydrogen donor is, for example, a system comprising 2-propanol and a base, or, most preferably, HOOCH in the presence of an amine, such as triethylamine or ammonia. The hydrogen donor may also be used as inert solvent, especially 2-propanol or most preferably HCOOH.

Step (b) can also be carried out by hydrogenating with hydrogen in the presence of a catalyst of formula (II d') or (II d"), respectively. A suitable inert solvent is, e.g. an ether, such as tetrahydrofuran, an ester, such as ethylacetate, or an alcohol, such as a $C_1$–$C_4$alkanol, for example, isopropanol.

Preferred Hal is chloro.

In a variation of Step (b), when a chiral Ru(II) catalyst of formula (II d'''')

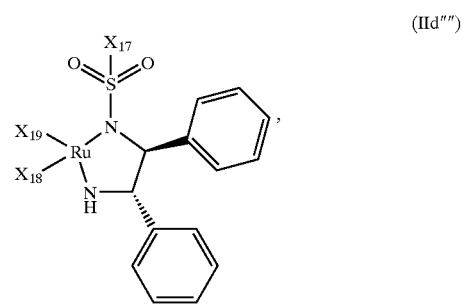

(IId'''')

wherein $X_{17}$ represents an aliphatic, cycloaliphatic, cycloaliphatic-aliphatic, aryl or araliphatic residue; and $X_{18}$ represents an aliphatic, cycloaliphatic, cycloaliphatic-aliphatic, aryl or araliphatic residue; and $X_{19}$ is hydrogen, and using isopropanol as the hydrogen donor system, e.g. in a temperature range of 25° C. to 75° C., are used, a compound of formula (II e')

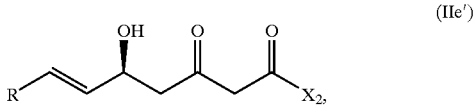

(IIe')

wherein R and $X_2$ have the meanings as defined above; is obtained. A compound of formula (II e') can then be reduced to obtain a corresponding compound of formula (II e) by using a chiral Ru(II) catalyst of formulae (II d), (II d'), (II d'') or (II d''') and an appropriate hydrogen donor system, especially $HCOOH/N(C_2H_5)_3$.

It has surprisingly been found that the reduction in Step (b) results in syn diols of formula (II e). It is known from the art that the reduction of a 1,3-diketone under asymmetric transfer hydrogenation conditions would normally lead to the corresponding anti-diol derivatives, when using a chiral Ru(II) catalyst ("Noyori catalyst"). (see Cossy et al., Tetrahedron Lett. 2001, 42, 5005).

Accordingly, the present invention likewise relates to process Step (b).

The preferred syn/anti relation of resulting compounds of formula (II e) is, for example, 90:10, preferably 95:5, most preferably ≧99.

Step (c):

The saponification Step (c) is carried out, for example, by treating the ester of formula (II d) with a strong base, such as an alkali metal hydroxide, preferably NaOH, or with $Ca(OH)_2$ and acidifying the resulting reaction mixture.

Step (d):

The isolation Step (d) of a compound of formula (I) is carried out according to conventional isolation methods, such as by crystallizing the resulting compound of formula (I) from the reaction mixture or by chromatography of the reaction mixture.

Inert solvents are those that do not react with the corresponding reactants.

The conversion of an acid of formula (I) into a salt is carried out in a manner known per se.

Thus, for example, a salt with a base of compounds of the formula I is obtained by treating with a base. Salts can be converted into the free compounds in a customary manner, and salts with a base can be converted, for example, by treating with a suitable acid agent to the free acid.

The conversion of an acid of formula (I) into a corresponding lactone of formula (I a) or (I b), respectively, is carried out in the presence of an acid, preferably a mineral acid, in a suitable, e.g. protic or aproctic, solvent, such as ethanol or acetonitrile. Depending on the acid, the conversion is carried out in a temperature range, for example, from −78° to the boiling point of the solvent. Most preferably, $H_3PO_4$ in acetonitrile at 60° C. is used.

The conversion of a lactone of formula (I a) or (I b), respectively, into a salt of the acid of formula (I) is carried out, for example, in a mixture of a protic solvent, e.g. ethanol, and water, by using an alkalimetall hydroxide, such as LiOH, NaOH or $Ca(OH)_2$. Alternatively, the lactone can be hydrolysed by using an alkalimetall hydroxide, such as LiOH, NaOH and the resulting salt can be converted into the calcium salt of the acid of pitavastatin by addition of an aqueous solution of $CaCl_2$ in water.

A variant to the process according to the present invention comprises the direct formation of a lactone of a compound of formula (I). The formation of said lactone can be carried out by treating a compound of formula (I) or (II e) with an acid, such as a mineral acid, preferable with $H_3PO_4$.

The conversion of a resulting compound of formula (I) wherein the element ⋯ represents —CH=CH— into a compound of formula (I) wherein the element ⋯ represents —$CH_2$—$CH_2$— is carried out by selectively hydrogenating the double bond —CH=CH—, especially with an appropriate reduction agent, for example, by catalytic hydrogenation in the presence of a hydrogenation catalyst, for example, a Ruthenium catalyst, such as (Ru(cod)(nu-3-(2-methylally))2, by reduction with hydrogen in the presence of a hydrogenation catalyst or with a hydride, for example, a hydride which, if desired, may be complex, such as a hydride formed from an element of the 1st and 3rd main groups of the periodic table of the elements, for example borohydride or aluminohydride, for example lithium borohydride, lithium aluminium hydride, diisobutylaluminium hydride (an additional reduction step using alkali metal cyanoborohydride, such as sodium cyanoborohydride, may be necessary), and also diborane.

Instead of converting a resulting compound of formula (I) wherein the element ⋯ represents —CH=CH— into a compound of formula (I) wherein the element ⋯ represents —$CH_2$—$CH_2$—, the hydrogenation of the double bond —CH=CH— can be effected, with compounds of formulae (II c) or (II e), e.g. in addition to reaction steps (a) or (b), respectively.

The present invention likewise relates to a compound of formulae (II d), (II d'), (II d''), and (II d''')

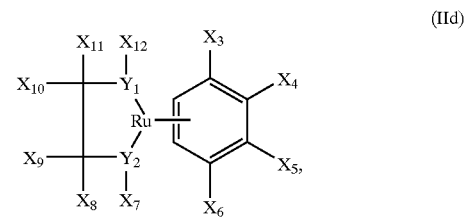

(IId)

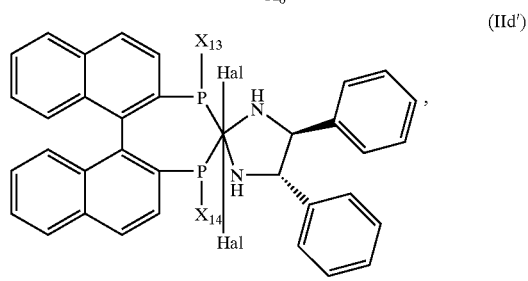

(IId')

-continued

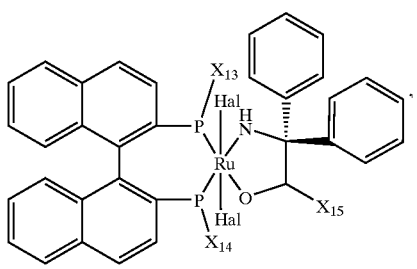

(IId″)

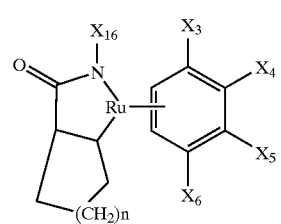

(IId‴)

wherein $X_3$, $X_4$, $X_5$, and $X_6$, independently of one another, represents hydrogen, $C_1$–$C_7$alkyl, an araliphatic or aryl residue; one of $X_7$ and $X_{12}$ represents hydrogen, an aliphatic, cycloaliphatic, cycloaliphatic-aliphatic, aryl or araliphatic residue, araliphatyloxy, or araliphatylamino; and the other represents $SO_2$—$X_7'$ in which $X_7'$ is an aliphatic, cycloaliphatic, cycloaliphatic-aliphatic, aryl or araliphatic residue, araliphatyloxy, or araliphatylamino; $X_8$, $X_9$, $X_{10}$, and $X_{11}$, independently of one another, represent hydrogen, an aliphatic or cycloaliphatic residue, an araliphatic residue, aryl, acyl, aliphatyl-sulfonyl, or arylsulfonyl; Hal is halogen; $Y_1$ and $Y_2$ are nitrogen, or independently of one another, $Y_1$—$X_{12}$ and $Y_2$—$X_7$ may be replaced by oxygen; $X_{13}$, and $X_{14}$, independently of one another, represents an aliphatic, a cycloaliphatic, a cycloaliphatic-aliphatic, an aryl or araliphatic residue; $X_{15}$ represents hydrogen, $C_1$–$C_7$alkyl, a cycloaliphatic, a cycloaliphatic-aliphatic, an araliphatic or an aryl residue; $X_{16}$ represents an aliphatic, a cycloaliphatic, a cycloaliphatic-aliphatic, an aryl or araliphatic residue or represents the structural element of formula $CH(X_{16}')(X_{16}'')$, wherein $X_{16}'$ represents $C_1$–$C_7$alkyl, an aryl or an araliphatic or a heteroaryl residue and $X_{16}''$ represents $C_1$–$C_7$alkyl, an aryl or an araliphatic residue or represents hydoxy, amino or mono- or di-substituted amino; and wherein, in each case, any (hetero)aromatic residue of a compound of formulae (II d), (II d'), (II d″) and (II d‴) is unsubstituted or substituted.

The process for the manufacture of compounds of formula (I) and salts thereof can be, for example, illustrated by means of the following reaction scheme for the manufacture of pitavastatin:

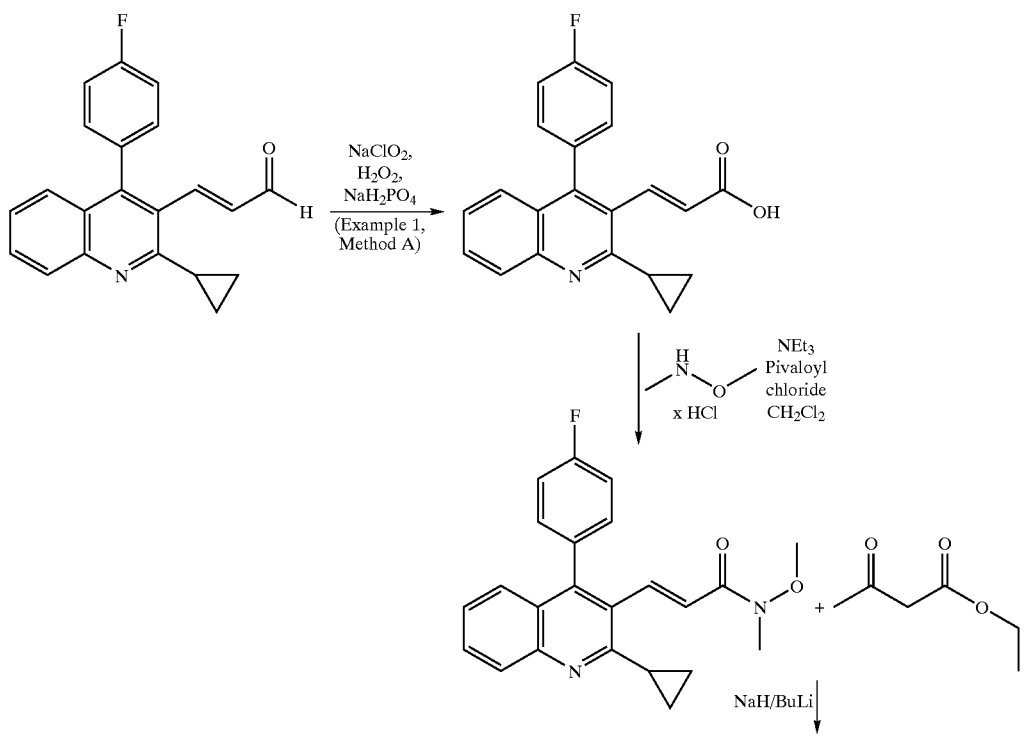

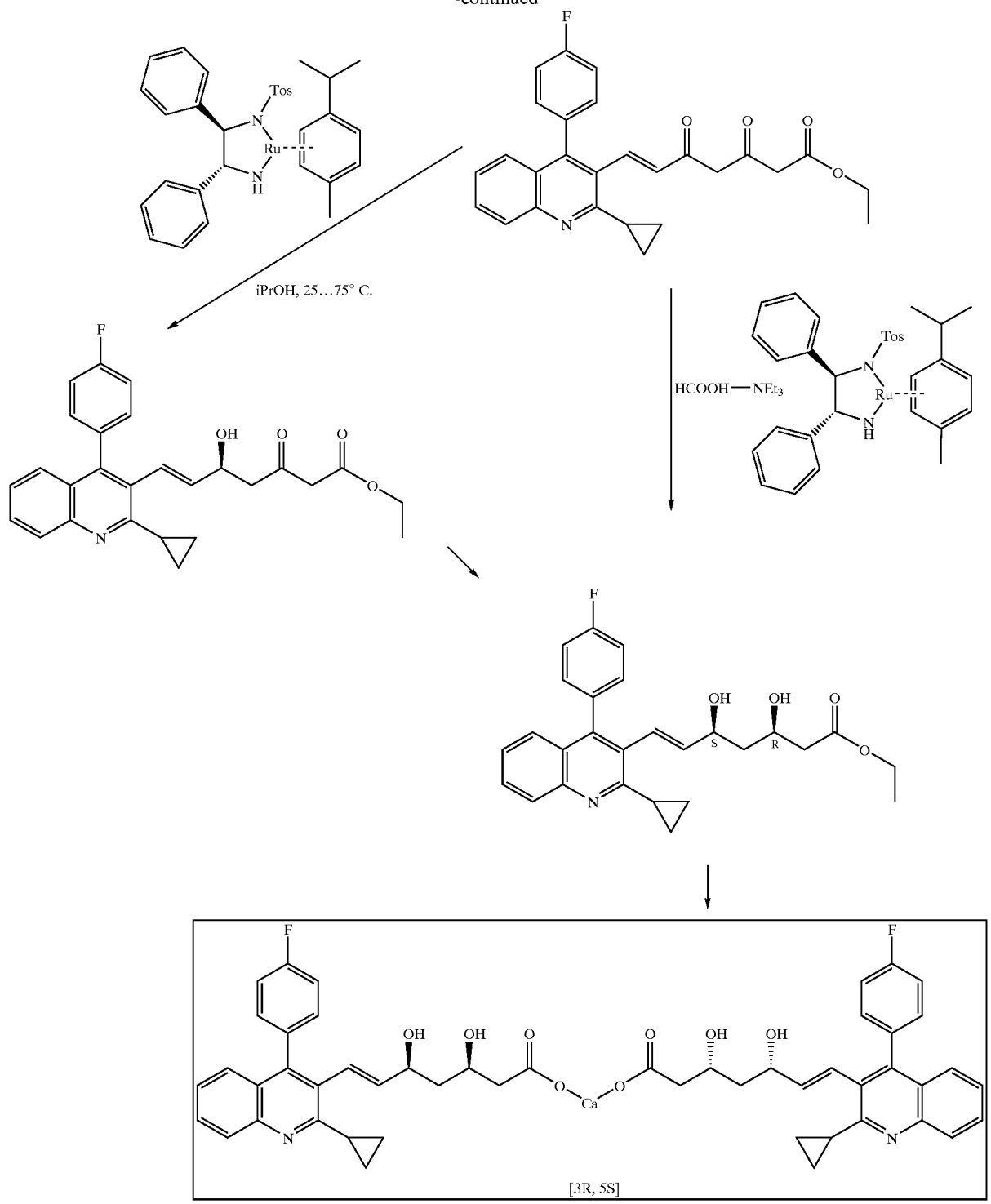

The present invention likewise relates to the novel compounds, e.g. starting materials or intermediates, respectively, as described in the Working Examples part.

Especially, the present invention likewise relates to a compound of formula (I) or a salt thereof or a lactone thereof, wherein the element ≡ represents —CH$_2$—CH$_2$— or —CH=CH— and R represents a cyclic residue, directly obtained or obtainable by the process according to the present invention.

The invention is illustrated by the following Examples.

EXAMPLE SECTION

Manufacture of Starting Material

The starting material can be manufactured, for example, as follows:

Example 1

Preparation of (E)-3-[2-Cyclopropyl-4-(4-fluoro-phenyl)-quinolin-3-yl]-acrylic acid (Method A)

To a mixture of (E)-3-[2-Cyclopropyl-4-(4-fluoro-phenyl)-quinolin-3-yl]-propenal (50.0 g, 157.5 mmol) in acetonitrile (650 ml) and sodium dihydrogenphosphate (30.5 g, 220.5 mmol) in water (100 ml) is added hydrogen peroxide (18.8 g, 165.4 mmol) and a solution of sodium chlorite (25.0 g, 220.5 mmol) in water (120 ml) at 0° C. The reaction mixture is stirred in an ice bath for 120 min. Sodium thiosulfate pentahydrate (2.5 g, 10 mmol) and then 2M hydrochloric acid is added to adjust the pH to 2–3. After dilution with ethyl acetate (200 ml), the organic phase is separated and the pH of the aq. phase adjusted to 3–4 by addition of 2M sodium hydroxide. The reaction mixture is partitioned between ethyl acetate and water. The organic phases are separated, dried over magnesium sulphate and evaporated to afford (E)-3-[2-cyclopropyl-4-(4-fluoro-phenyl)-quinolin-3-yl]-acrylic acid. MS (ES): [M–H]– 332, Mp. 173–174° C.

Preparation of (E)-3-[2-Cyclopropyl-4-(4-fluoro-phenyl)-quinolin-3-yl]-acrylic acid (Method B)

To a mixture of diisopropylamine (2.42 g, 24.0 mmol) and 8.88 ml (24.0 mmol) butyllithium (2.7M in Heptan) in THF (20 ml) at –70° C. is added a soln. of crotonic acid (1.03 g, 12.0 mmol) in THF (10.0 ml). After stirring at –70° C. and 0° C., a soln. of cyclopropanecarboxylic acid N,O-dimethylhydroxyamide (1.29 g, 10.0 mmol) in THF (10.0 ml) is added. The solution is heated to 48° C. After cooling to –50° C., a solution of glacial acetic acid (5 ml) in THF (10 ml), and 20% aq. NaCl (25 ml) are slowly added. The pH is adjusted to 1.5 with 2M HCl and the mixture is extracted with CH$_2$Cl$_2$ (3×25 ml). Organic phases are washed with 20% aqeous NaCl (2×25 ml) and evaporated to dryness under reduced pressure. The resulting yellow oil is dissolved in toluene (100 ml). 4-Fluoro-2'-aminobenzophenone methansulfonic acid salt (3.23 g, 10.4 mmol) is added and the solution is refluxed in a water separator apparatus for 24 h. Upon cooling, a brown precipitate is formed, which is separated from the mother liquor and purified by chromatography on silica gel (CH$_2$Cl$_2$—MeOH) to afford (E)-3-[2-cyclopropyl-4-(4-fluoro-phenyl)-quinolin-3-yl]-acrylic acid. MS (ES): [M–H]– 332.

This reaction step is illustrated by the following reaction scheme:

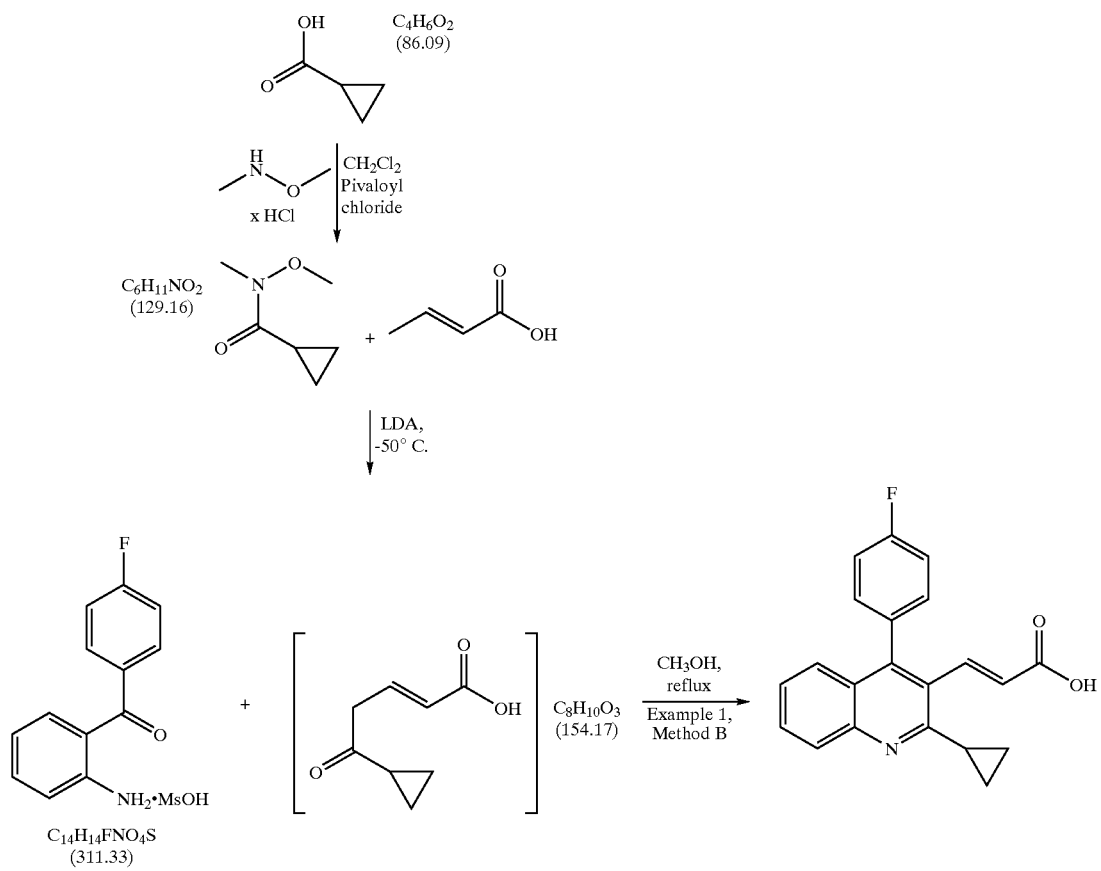

Example 2

Preparation of (E)-3-[2-Cyclopropyl-4-(4-fluoro-phenyl)-quinolin-3-yl]-N-methoxy-N-methyl-acrylamide To a solution of (E)-3-[2-Cyclopropyl-4-(4-fluoro-phenyl)-quinolin-3-yl]-acrylic acid (2.0 g, 6.0 mmol) in dichloromethane (25 ml) at –5° C. is added triethylamine (0.668 g, 6.6 mmol).and pivaloyl chloride (0.725 g, 6.0 mmol). After stirring at 0° C. for 170 min, N,O-dimethyl-hydroxylamine hydrochloride (0.59 g, 6.0 mmol) and triethylamine (1.22 g, 12.0 mmol) are added. After stirring in an ice bath for 90 min, and at room temperature for 30 min, more N,O-dimethylhydroxylamine hydrochloride (0.177 g, 1.8 mmol) is added and the reaction is stirred at room temperature for 17 h. After quenching with 0.2M citrate buffer pH5 (25 ml), the organic phase is separated and washed with 0.2M citrate buffer pH5 (25 ml), 0.2M phosphate buffer pH7 (25 ml) and water (25 ml). The water phases are extracted with dichloromethane (2×20 ml). Combined organic phases are dried over magnesium sulphate, evaporated, and the crude product chromatographed on silica gel (hexane/ethyl acetate 2:1) to afford (E)-3-[2-cyclopropyl-4-(4-fluoro-phenyl)-quinolin-3-yl]-N-methoxy-N-methyl-acrylamide (7). MS (ES): [M+H]+ 377, Mp. 155–156° C.

Example 3

Preparation of (S)-Phenylethyl Acetoacetamide

To a boiling p-xylene solution (1000 ml), a solution of (S)-phenylethylamine (12.1 g, 100.0 mmol) and 2,2,6-trimethyl-4H-1,3-dioxin-4-one (14.2 g, 100.0 mmol) in p-xylene (500 ml) is added dropwise at reflux temperature over a period of 60 min. During this time, 400 ml of solvent were distilled off at athmosperic pressure. The solution is stirred another 45 min at reflux, whereupon 450 ml of solvent were distilled off. TLC shows complete conversion of starting material. The reaction mixture is taken to dryness under reduced pressure and dried for 20 h at high vacuum. The crude product is chromatographed on silica gel (hexane/ethyl acetate 1:2) to afford (S)-phenylethyl acetoacetamide as a yellow oil (solidifies upon standing in the refrigerator). MS (ES): [M+H]+ 206.

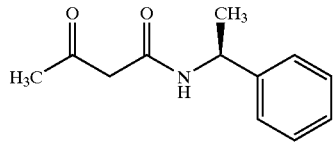

WORKING EXAMPLES

Example 1

(a) Preparation of (E)-7-[2-Cyclopropyl-4-(4-fluoro-phenyl)-quinolin-3-yl]-3,5-dioxo-hept-6-enoic acid ethyl ester To a suspension of sodium hydride (100 mg, 4.17 mmol) in tetrahydrofurane (4 ml) under argon is added at −5° C. ethyl acetoacetate (546 mg, 4.19 mmol), butyllithium (n-heptane solution (soln.), 1.55 ml, 4.19 mmol), and a solution of 3-[2-cyclopropyl-4-(4-fluoro-phenyl)-quinolin-3-yl]-N-methoxy-N-methyl-acrylamide in tetrahydrofurane (9 ml). After 5 h stirring at room temperature, the reaction mixture is added to a suspension of sodium hydride (200 mg, 8.33 mmol), ethyl acetoacetate (1.09 g, 8.39 mmol), and butyllithium (n-heptane soln., 3.1 ml, 8.37 mmol) in tetrahydrofurane (8 ml) at −5 to 0° C. After 60 minutes at 0° C., acetic acid (100%, 2.25 g, 37.5 mmol), 25% aq. NaCl (5 ml), and water (3 ml) are added and the mixture is stirred vigorously for 10 min. The (upper) organic phase is successively washed with 25% aq. NaCl (5 ml) and water (5 ml), and evaporated to dryness under reduced pressure. The residue is dried under vacuum at 40° C. and purified by silica gel chromatography (hexane/ethyl acetate 3:1) to give (E)-7-[2-cyclopropyl-4-(4-fluoro-phenyl)-quinolin-3-yl]-3,5-dioxo-hept-6-enoic acid ethyl ester, semisolid honey. MS (ES): [M+H]+ 446.

(a') Preparation of (E)-7-[2-Cyclopropyl-4-(4-fluoro-phenyl)-quinolin-3-yl]-3,5-dioxo-hept-6-enoic acid diethyl amide To a suspension of sodium hydride (600 mg, 25.0 mmol) in tetrahydrofurane (20 ml) under argon is added at −5° C. diethyl acetoacetamide (3.93 g, 25.0 mmol) in tetrahydrofurane (2.0 ml), tetrahydrofurane (22.0 ml), butyllithium (n-heptane solution, 9.2 ml, 25.0 mmol), and a solution of 3-[2-cyclopropyl-4-(4-fluoro-phenyl)-quinolin-3-yl]-N-methoxy-N-methyl-acrylamide (4.51 g, 12.0 mmol) in tetrahydrofurane (40 ml). After 1 h stirring at −5 to 0° C., acetic acid (4.4 g, 73.3 mmol), 25% aq. NaCl (10 ml), and water (10 ml) are added to the reaction mixture and the mixture is stirred vigorously for 10 min. The (upper) organic phase is washed with 25% aq. NaCl (2×20 ml), the water phases are extracted with ethylacetate (25 ml) and the combined organic phases filtered and evaporated to dryness under reduced pressure. The residue is purified by silica gel chromatography (hexane/ethyl acetate 1:1) to give (E)-7-[2-cyclopropyl-4-(4-fluoro-phenyl)-quinolin-3-yl]-3,5-dioxo-hept-6-enoic acid diethyl amide. Mp. 97–105° C., MS (ES): [M+H]+ 473.

This reaction step is illustrated by the following reaction scheme:

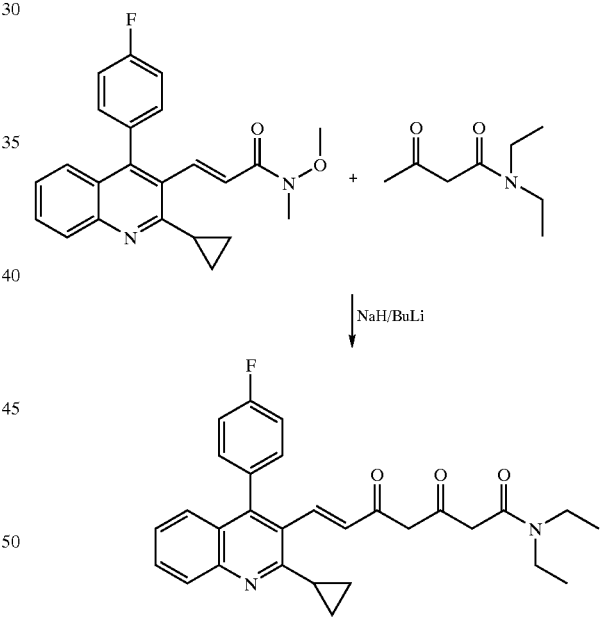

(a") Preparation of (S)-(E)-7-[2-Cyclopropyl-4-(4-fluoro-phenyl)-quinolin-3-yl]-3,5-dioxo-hept-6-enoic acid phenylethyl amide To a suspension of sodium hydride (1.24 g, 49.45 mmol) in tetrahydrofurane (40 ml) under argon is added at 0° C. (S)-phenylethyl acetoacetamide (10.15 g, 49.45 mmol) in tetrahydrofurane (30 ml) and tetrahydrofurane (10 ml). At −8° C., butyllithium (n-heptane solution, 36.63 ml, 98.9 mmol), and a solution of 3-[2-cyclopropyl-4-(4-fluoro-phenyl)-quinolin-3-yl]-N-methoxy-N-methyl-acrylamide (8.69 g, 23.08 mmol) in tetrahydrofurane (90 ml). After 2 h stirring at −10 to 0° C., acetic acid (17 ml, 296.7 mmol), 25% aq. NaCl (50 ml), and water (50 ml) are added to the reaction mixture and the mixture is stirred vigorously for 10 min. The (upper) organic phase is washed with 25% aq. NaCl (2×50 ml), the water phases are extracted with ethylacetate (50 ml) and the combined organic phases dried over anhydrous sodium sulfate and evaporated to dryness under reduced pressure. The residue is purified by silica gel chromatography (hexane/ethyl acetate 1:1) to give (S)-(E)-7-[2-cyclopropyl-4-(4-fluoro-phenyl)-quinolin-3-yl]-3,5-dioxo-hept-6-enoic acid phenylethyl amide. Mp. 124–127° C., MS (ES): [M+H]+ 521.

This reaction step is illustrated by the following reaction scheme:

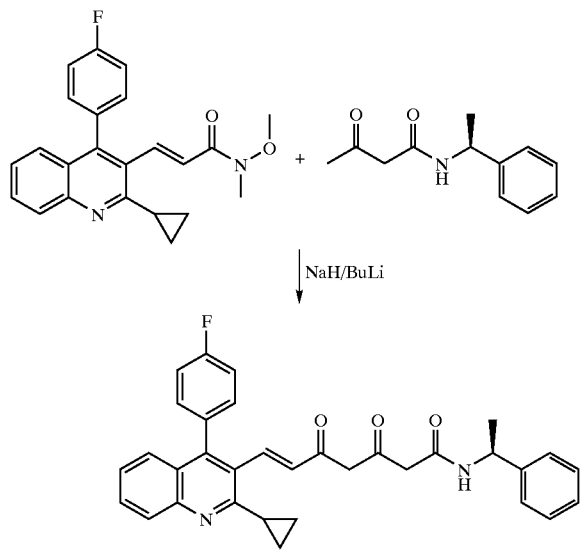

(b) Preparation of (E)-(5S)-7-[2-Cyclopropyl-4-(4-fluoro-phenyl)-quinolin-3-yl]-5-hydroxy-3-oxo-hept-6-enoic acid ethyl ester (9)

To a solution of (E)-7-[2-cyclopropyl-4-(4-fluoro-phenyl)-quinolin-3-yl]-3,5-dioxo-hept-6-enoic acid ethyl ester (740 mg, 1.66 mmol) in dry isopropanol (30 ml) under argon is added (1R,2R)-N-p-toluenesulfonyl-1,2-diphenylethylenediamine-Ru$^{III}$-p-cymene complex

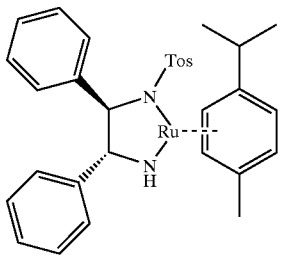

[K.-J. Haack, S. Hashiguchi, A. Fujii, T. Ikariya, R. Noyori; *Angew. Chem. Int. Ed. Engl.* 1997, 36, 285] (50 mg, 0.083 mmol). The red suspension is stirred at ambient temperature for 13 hours and at 50° C. for 96 hours. Evaporation of the reaction mixture under reduced pressure, followed by silica gel chromatography (hexane/ethyl acetate 3:1) of the dried residue affords (E)-(S)-7-[2-cyclopropyl-4-(4-fluoro-phenyl)-quinolin-3-yl]-5-hydroxy-3-oxo-hept-6-enoic acid ethyl ester. MS (EI): [M+]447, enantiomeric purity (S/R): 92.7/7.3% (HPLC on ChiralPak AD-column).

(c) Preparation of (E)-(3R,5S)-7-[2-Cyclopropyl-4-(4-fluoro-phenyl)-quinolin-3-yl]-3,5-dihydroxy-hept-6-enoic acid ethyl ester To a solution of (E)-7-[2-cyclopropyl-4-(4-fluoro-phenyl)-quinolin-3-yl]-3,5-dioxo-hept-6-enoic acid ethyl ester (600 mg, 1.347 mmol) in N,N-dimethylformamide (5 ml) under argon is added (1R,2R)-N-p-toluenesulfonyl-1,2-diphenylethylenediamine-Ru$^{II}$-pcymene complex [cf. above] (40 mg, 0.067 mmol) and formic acid-triethylamine 5:2 (v/v)-mixture (2 ml). After stirring at 50° C. for 30 min, triethylamine (4.7 ml, 33.79 mmol) is added to the orange, clear solution, and stirring is continued at 50° C. for 19 hours. Evaporation of the reaction mixture under reduced pressure, followed by silica gel chromatography (toluene/ethyl acetate 3:1) of the dried residue affords (E)-(3R,5S)-7-[2-Cyclopropyl-4-(4-fluoro-phenyl)-quinolin-3-yl]-3,5-dihydroxy-hept-6-enoic acid ethyl ester. MS (EI): [M+]447, diastereomeric purity (syn/anti): 90.0/10.0%, enantiomeric purity (3R5S/3S5R): 80.0/20.0% (HPLC on ChiralPak AD-column).

(d) Preparation of (E)-(3R,5S)-7-[2-cyclopropyl-4-(4-fluoro-phenyl)-quinolin-3-yl]-3,5-dihydroxy-hept-6-enoic acid calcium salt To a solution of diol (E)-(3R,5S)-7-[2-cyclopropyl-4-(4-fluoro-phenyl)-quinolin-3-yl]-3,5-dihydroxy-hept-6-enoic acid ethyl ester (940 mg, 2.09 mmol) in EtOH (5 ml) is added an aquous solution of NaOH (10 ml, 1 M) and the resulting suspension is stirred until the ester disappeared. After completion of the hydrolysis aqueous HCl (15 ml, 1 M) is added and the solvent is removed in vaccuum. Then CH$_2$Cl$_2$ (10 ml) is added and the organic layer is separated. The aqueous layer is extracted with CH$_2$Cl$_2$ (2×30 ml) and the combined organic extracts are removed in vaccum. The residue is dissolved in H$_2$O (20 ml) and a solution of CaCl$_2$ (8 ml, 0.1 M) is added dropwise. The reaction solution is stirred overnight and the resulting white precipitate is collected by filtration to obtain (E)-(3R,5S)-7-[2-cyclopropyl-4-(4-fluoro-phenyl)-quinolin-3-yl]-3,5-dihydroxy-hept-6-enoic acid calcium salt.

What is claimed is:

1. A process for the manufacture of compound of formula (II e)

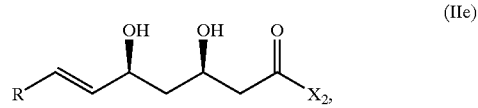

wherein R represents a cyclic residue, and X$_2$ represents substituted hydroxy or substituted amino; comprising reducing a compound of formula (II c)

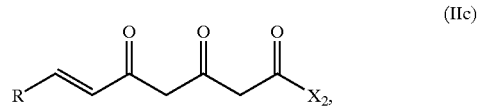

wherein R and X$_2$ have the meanings as defined above; in the presence of a hydrogen donor and a chiral Ru(II) catalyst selected from the group consisting of a compound of formulae (II d), (II d'), (II d"), and (II d''')

(IId)

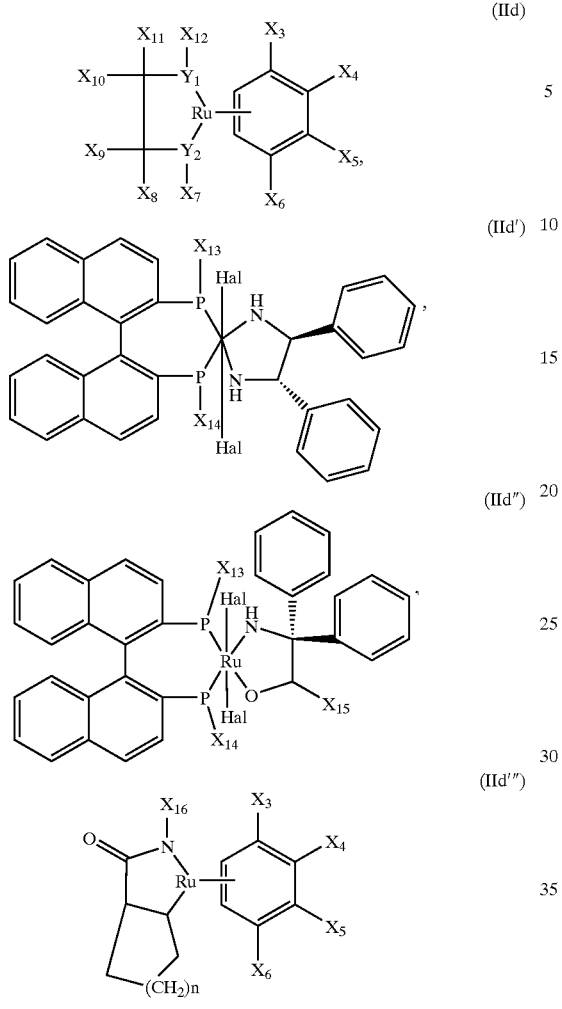

wherein $X_3$, $X_4$, $X_5$, and $X_6$, independently of one another, represents hydrogen, $C_1$–$C_7$alkyl, an araliphatic or aryl residue; one of $X_7$ and $X_{12}$ represents hydrogen, an aliphatic, cycloaliphatic, cycloaliphatic-aliphatic, aryl or araliphatic residue, araliphatyloxy, or araliphatylamino; and the other represents $SO_2$—$X_7'$ in which $X_7'$ is an aliphatic, cycloaliphatic, cycloaliphatic-aliphatic, aryl or araliphatic residue, araliphatyloxy, or araliphatylamino; $X_8$, $X_9$, $X_{10}$, and $X_{11}$, independently of one another, represents hydrogen, an aliphatic or cycloaliphatic residue, an araliphatic residue, aryl, acyl, aliphatyl-sulfonyl, or arylsulfonyl; Hal is halogen; $Y_1$ and $Y_2$ are nitrogen, or independently of one another, $Y_1$—$X_{12}$ and $Y_2$—$X_7$ may be replaced by oxygen; $X_{13}$, and $X_{14}$, independently of one another, represents an aliphatic, a cycloaliphatic, a cycloaliphatic-aliphatic, an aryl or araliphatic residue; $X_{15}$ represents hydrogen, $C_1$–$C_7$alkyl, a cycloaliphatic, a cycloaliphatic-aliphatic, an araliphatic or an aryl residue; $X_{16}$ represents an aliphatic, a cycloaliphatic, a cycloaliphatic-aliphatic, an aryl or araliphatic residue or represents the structural element of formula $CH(X_{16}')(X_{16}'')$, wherein $X_{16}'$ represents $C_1$–$C_7$alkyl, an aryl or an araliphatic or a heteroaryl residue and $X_{16}''$ represents $C_1$–$C_7$alkyl, an aryl or an araliphatic residue or represents hydoxy, amino or mono- or di-substituted amino; and wherein, in each case, any (hetero)aromatic residue of a compound of formulae (II d), (II d'), (II d"), and (II d''') is unsubstituted or substituted.

2. A process according to claim 1, wherein the chiral Ru(II) catalyst is a compound of formula (II d)

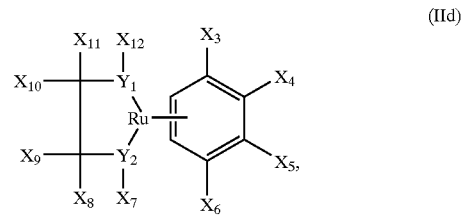

wherein $X_3$, $X_4$, $X_5$, and $X_6$, independently of one another, represents hydrogen, $C_1$–$C_7$alkyl, an araliphatic or aryl residue; one of $X_7$ and $X_{12}$ represents hydrogen, an aliphatic, cycloaliphatic, cycloaliphatic-aliphatic, aryl or aliphatic residue, araliphatyloxy, or araliphatylamino; and the other represents $SO_2$—$X_7'$ in which $X_7'$ is an aliphatic, cycloaliphatic, cycloaliphatic-aliphatic, aryl or araliphatic residue, araliphatyloxy, or araliphatylamino; $X_8$, $X_9$, $X_{10}$, and $X_{11}$, independently of one another, represents hydrogen, an aliphatic or cycloaliphatic residue, an araliphatic residue, aryl, acyl, aliphatyl-sulfonyl, or arylsulfonyl; Hal is halogen; and $Y_1$ and $Y_2$ are nitrogen.

3. A process according to claim 2, wherein the cyclic residue R is selected from the group consisting of

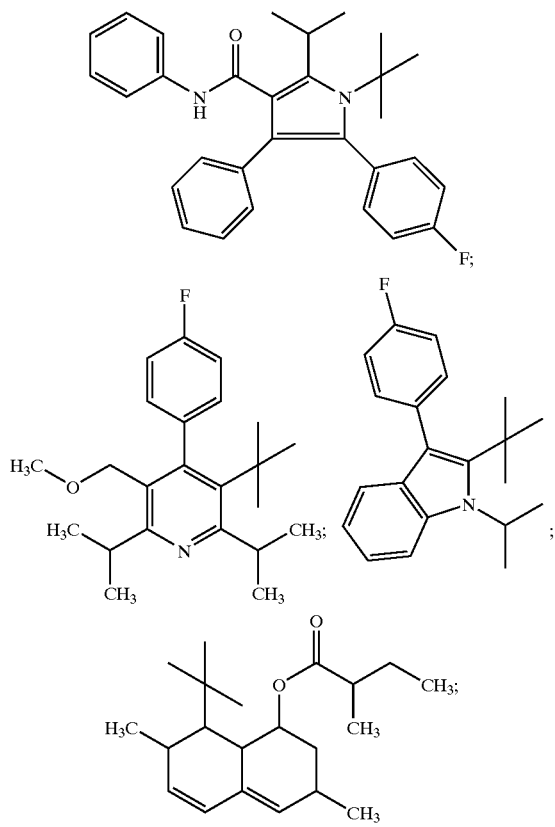

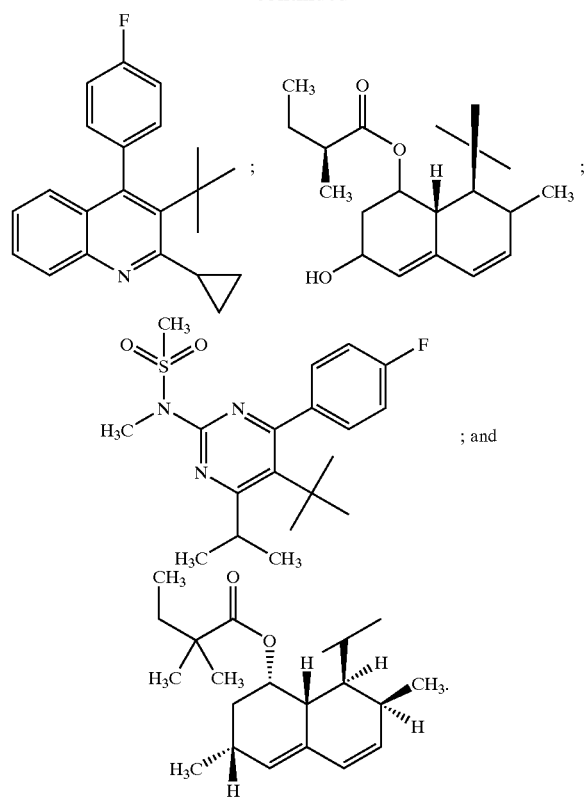
4. A process according to claim 3, wherein the cyclic residue R is
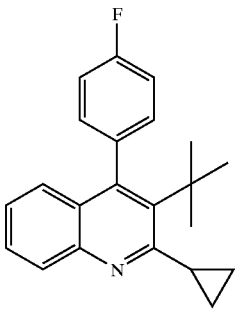
5. A process according to claim 1, wherein the hydrogen donor is HCOOH in the presence of ammonia or triethylamine.
6. A process according to claim 1, wherein the cyclic residue R is selected from the group consisting of
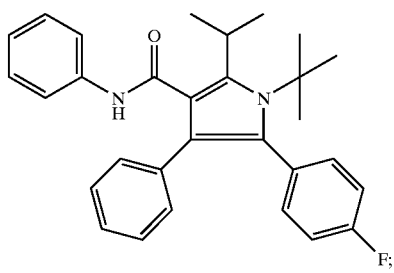
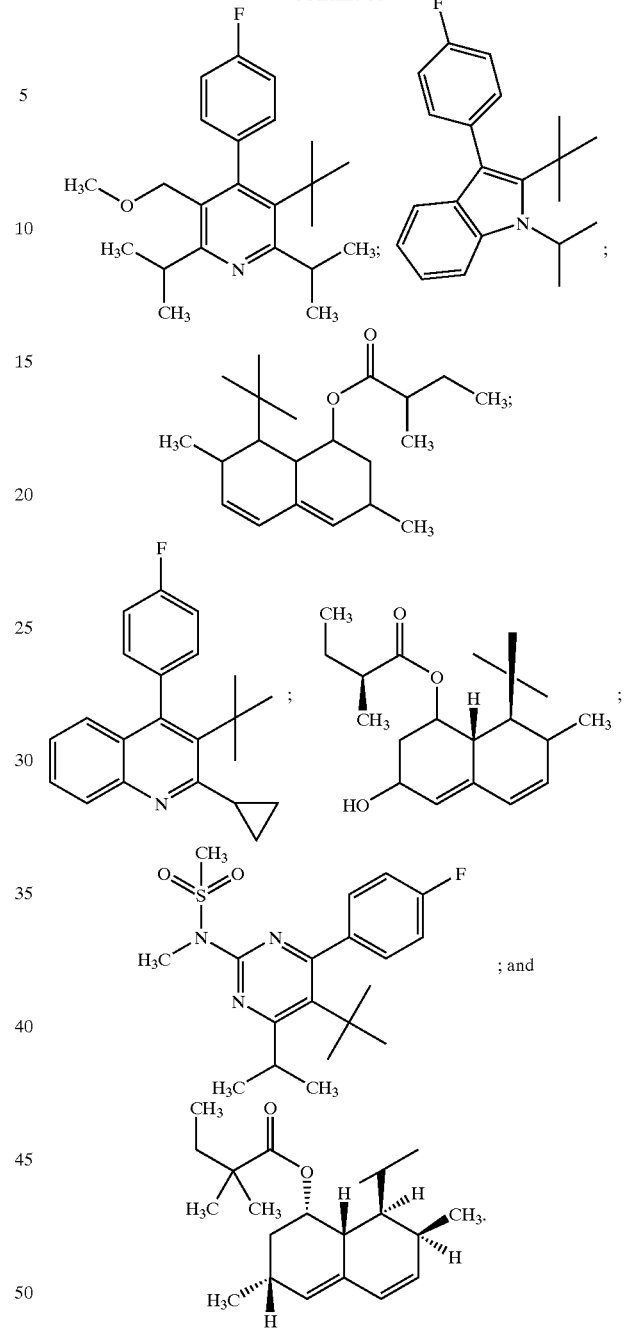
7. A process according to claim 6, wherein the cyclic residue R is
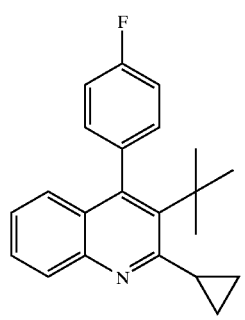

8. A process according to claim 1, which process further comprises
(a) hydrolysing a resulting compound of formula (II e)

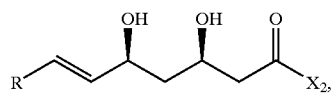
(IIe)

wherein R and $X_2$ have the meanings as defined above, to afford a compound of formula (I)

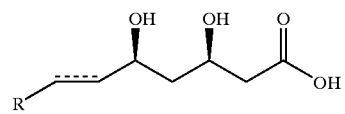
(I)

wherein R has the meaning as defined above; and
(b) isolating a resulting compound of formula (I), or a salt thereof;
and, if desired, converting a resulting free acid of formula (I) into a salt thereof, or into a lactone of formula (I a) or (I b), respectively, or converting a resulting lactone of a formula (I a) or (I b) into an acid of formula (I), or a salt thereof, or converting a resulting compound of formula (I) wherein the element ⁝⁝⁝⁝ represents —CH=CH— into a compound of formula (I) wherein the element ⁝⁝⁝⁝ represents —CH$_2$—CH$_2$—.

9. A process according to claim 8, wherein a compound of formula (II c) is prepared by a process comprising reacting a compound of formula (II a)

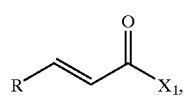
(IIa)

wherein R has the meaning as defined above and $X_1$ is an amino group substituted by $C_1$–$C_7$alkyl and $C_1$–$C_7$alkoxy; in the presence of a base with a compound of formula (II b)

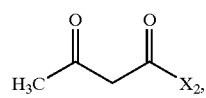
(IIb)

wherein $X_2$ has the meaning as defined above.

10. A process according to claim 9, wherein $X_2$ in a compound of formulae (II b), (II c) and (II e) represents substituted amino.

11. A process according to claim 9, wherein the cyclic residue R is selected from the group consisting of

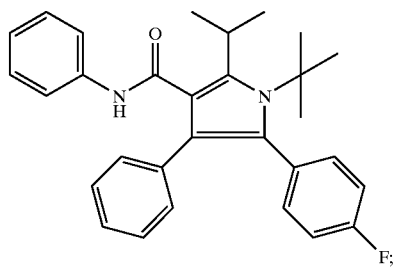

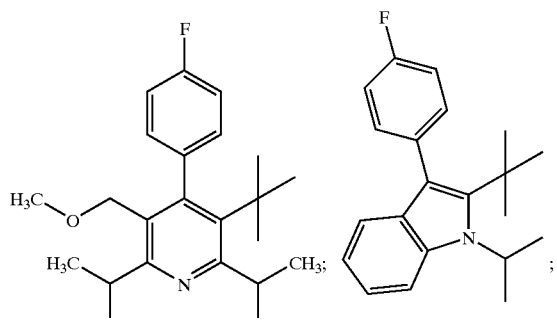

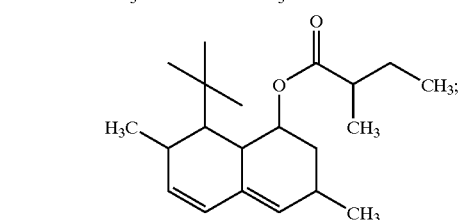

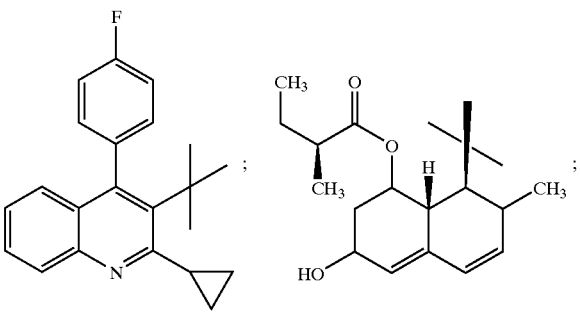

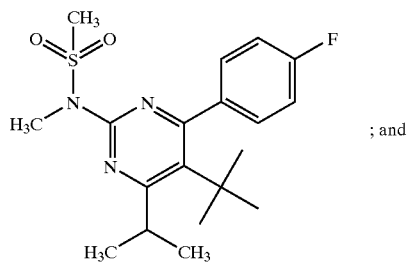

; and

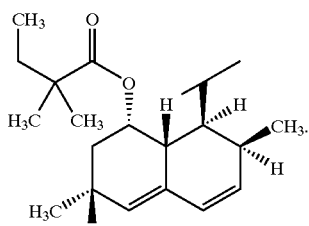

12. A process according to claim 11, wherein the chiral Ru(II) catalyst is a compound of formula (II d)

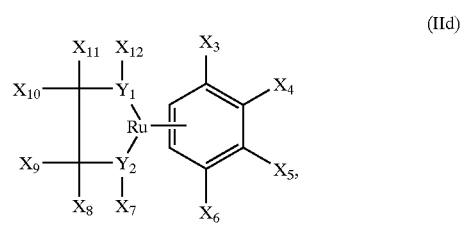
(IId)

wherein $X_3$, $X_4$, $X_5$, and $X_6$, independently of one another, represents hydrogen, $C_1$–$C_7$alkyl, an araliphatic or aryl residue; one of $X_7$ and $X_{12}$ represents hydrogen, an aliphatic, cycloaliphatic, cycloaliphatic-aliphatic, aryl or araliphatic residue, araliphatyloxy, or araliphatylamino; and the other represents $SO_2$—$X_7'$ in which $X_7'$ is an aliphatic, cycloaliphatic, cycloaliphatic-aliphatic, aryl or araliphatic residue, araliphatyloxy, or araliphatylamino; $X_8$, $X_9$, $X_{10}$, and $X_{11}$, independently of one another, represents hydrogen, an aliphatic or cycloaliphatic residue, an araliphatic residue, aryl, acyl, aliphatyl-sulfonyl, or arylsulfonyl; Hal is halogen; and $Y_1$ and $Y_2$, are nitrogen.

13. A process according to claim 11, wherein the cyclic residue R is

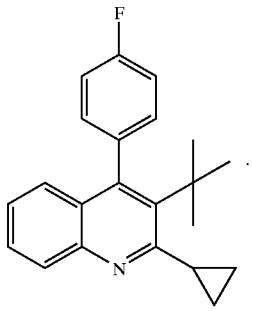

14. A process according to claim 13, wherein the chiral Ru(II) catalyst is a compound of formula (II d)

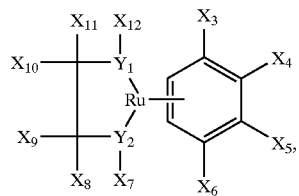

(IId)

wherein $X_3$, $X_4$, $X_5$, and $X_6$, independently of one another, represents hydrogen, $C_1$–$C_7$alkyl, an araliphatic or aryl residue; one of $X_7$ and $X_{12}$ represents hydrogen, an aliphatic, cycloaliphatic, cycloaliphatic-aliphatic, aryl or araliphatic residue, araliphatyloxy, or araliphatylamino; and the other represents $SO_2$—$X_7'$ in which $X_7'$ is an aliphatic, cycloaliphatic, cycloaliphatic-aliphatic, aryl or araliphatic residue, araliphatyloxy, or araliphatylamino: $X_8$, $X_9$, $X_{10}$, and $X_{11}$, independently of one another, represents hydrogen, an aliphatic or cycloaliphatic residue, an araliphatic residue, aryl, acyl, aliphatyl-sulfonyl, or arylsulfonyl; Hal is halogen; and $Y_1$ and $Y_2$, are nitrogen.

15. A process according to claim 14, wherein the hydrogen donor is HCOOH in the presence of ammonia or triethylamine.

* * * * *

UNITED STATES PATENT AND TRADEMARK OFFICE
CERTIFICATE OF CORRECTION

PATENT NO. : 6,909,003 B2  Page 1 of 2
APPLICATION NO. : 10/428257
DATED : June 21, 2005
INVENTOR(S) : Thomas Storz It is certified that error appears in the above-identified patent and that said Letters Patent is hereby corrected as shown below:

Column 7, please replace formula (IId'), beginning on line 22 with the following formula:

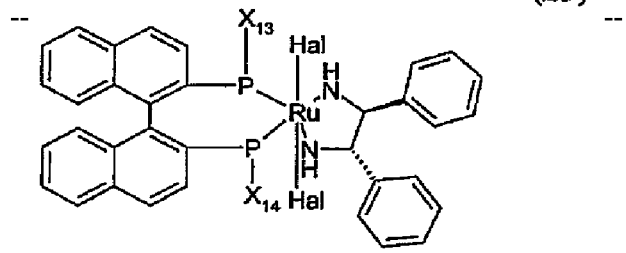

(IId')

Column 8, line 63 delete "phenyl C-$C_7$-alkynyl-", and replace with
--Phenyl $C_2$- $C_7$-alkynyl- --, Column 12, please replace the second formula (IId'), starting at line 57 with the following formula:

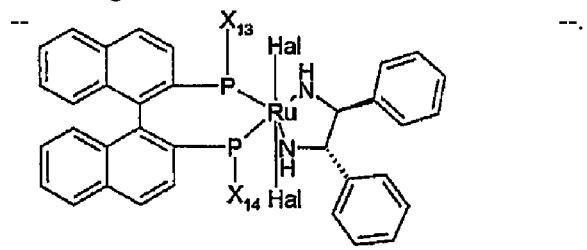

(IId')

Column 13, please replace formula (IId'''), starting at line 16 with the following formula:

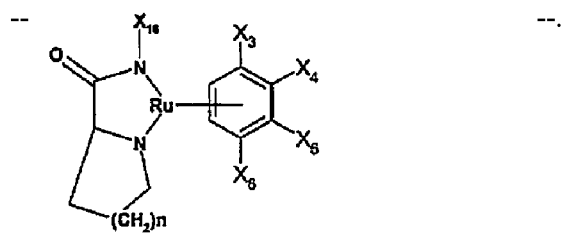

(IId''')

Column 22, line 9, please delete "pcymene" and replace with --p-cymene--.

UNITED STATES PATENT AND TRADEMARK OFFICE
CERTIFICATE OF CORRECTION

PATENT NO. : 6,909,003 B2
APPLICATION NO. : 10/428257
DATED : June 21, 2005
INVENTOR(S) : Thomas Storz Page 2 of 2

It is certified that error appears in the above-identified patent and that said Letters Patent is hereby corrected as shown below:

Claim 1, column 23 replace formula (IId"), starting on line 10 with the following formula:            (IId')
-- -- .

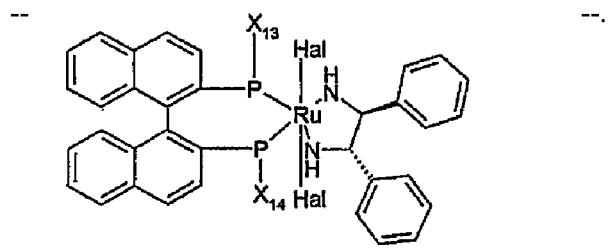

Claim 1, column 23, please replace formula (IId'''), starting on line 31 with the following formula:            (IId''')
-- --

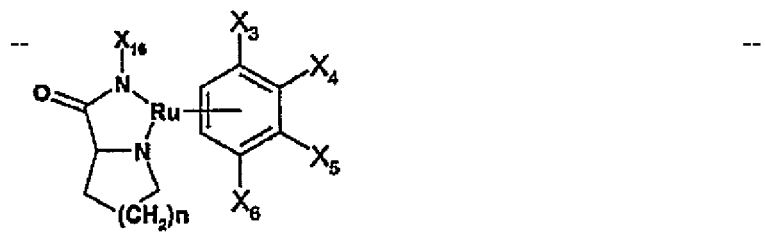

Signed and Sealed this

Twenty-fourth Day of April, 2007

JON W. DUDAS
*Director of the United States Patent and Trademark Office*